US008649577B1

(12) United States Patent
Arnold et al.

(10) Patent No.: US 8,649,577 B1
(45) Date of Patent: Feb. 11, 2014

(54) AUTOMATIC METHOD AND SYSTEM FOR MEASUREMENTS OF BONE DENSITY AND STRUCTURE OF THE HIP FROM 3-D X-RAY IMAGING DEVICES

(75) Inventors: Ben A. Arnold, Columbia, KY (US); Ping Xiang, Columbia, KY (US)

(73) Assignee: Image Analysis, Inc., Columbia, KY (US)

( * ) Notice: Subject to any disclaimer, the term of this patent is extended or adjusted under 35 U.S.C. 154(b) by 833 days.

(21) Appl. No.: 12/626,825

(22) Filed: Nov. 27, 2009

Related U.S. Application Data

(60) Provisional application No. 61/118,616, filed on Nov. 30, 2008, provisional application No. 61/118,619, filed on Nov. 30, 2008.

(51) Int. Cl.
G06K 9/00 (2006.01)
(52) U.S. Cl.
USPC .......................................................... 382/128
(58) Field of Classification Search
None
See application file for complete search history.

(56) References Cited

U.S. PATENT DOCUMENTS

| | | |
|---|---|---|
| 4,233,507 A | 11/1980 | Volz |
| 4,649,561 A | 3/1987 | Arnold |
| 4,663,772 A | 5/1987 | Mattson et al. |
| 4,724,110 A | 2/1988 | Arnold |
| 4,782,502 A | 11/1988 | Schulz |
| 4,870,666 A | 9/1989 | Lonn et al. |
| 4,922,915 A | 5/1990 | Arnold et al. |
| 4,985,906 A | 1/1991 | Arnold |
| 5,034,969 A | 7/1991 | Ozaki |
| 5,068,788 A | 11/1991 | Goodenough et al. |
| 5,222,021 A | 6/1993 | Feldman et al. |
| 5,235,628 A | 8/1993 | Kalendar |
| 5,335,260 A | 8/1994 | Arnold |
| 5,442,674 A | 8/1995 | Picard et al. |
| 5,521,955 A | 5/1996 | Gohno et al. |
| 5,577,089 A | 11/1996 | Mazess |
| 5,696,805 A | 12/1997 | Gaborski et al. |
| 5,712,892 A | 1/1998 | Weil et al. |
| 5,757,877 A | 5/1998 | Wilting |
| 5,774,519 A | 6/1998 | Lindstrom et al. |
| 5,782,762 A | 7/1998 | Vining |

(Continued)

OTHER PUBLICATIONS

Agatston, Arthur S. et al. Quantification of coronary artery calcium using ultrafast computed tomography, American College of Cardiology, 1990; 15: pp. 827-832.

(Continued)

Primary Examiner — John Pauls
Assistant Examiner — Trang Nguyen
(74) Attorney, Agent, or Firm — Jerry Turner Sewell

(57) ABSTRACT

A method uses a computer and software to measure bone density and structure of the proximal femur of the hip from a volumetric set of images containing pixels representing x-ray attenuation of the subject which are acquired with three-dimensional X-ray imaging devices. The method automatically locates anatomical markers of the hip without operator interaction, automatically positions regions of interest (ROIs) for measurement, automatically determines bone density measures of the ROIs, and automatically reports the results for individual subjects. Bone density measurements of ROIs include the integral bone of the total hip and neck as well as trabecular bone. The method automatically identifies a three-dimensional region-of-interest (ROI) volume which includes the hip, determines a three-dimensional coordinate system referenced to the anatomy of the subject, analyzes the ROI volume to identify voxels in the volume which satisfy defined criteria, and determines a measure of bone structure.

15 Claims, 17 Drawing Sheets

(56) References Cited

U.S. PATENT DOCUMENTS

| | | | |
|---|---|---|---|
| 5,891,030 | A | 4/1999 | Johnson et al. |
| 6,026,142 | A | 2/2000 | Gueziec et al. |
| 6,226,350 | B1 | 5/2001 | Hsieh |
| 6,233,304 | B1 | 5/2001 | Hu et al. |
| 6,243,437 | B1 | 6/2001 | Hu et al. |
| 6,278,761 | B1 | 8/2001 | Kim et al. |
| 6,302,582 | B1 | 10/2001 | Nord et al. |
| 6,320,931 | B1 | 11/2001 | Arnold |
| 6,421,552 | B1 | 7/2002 | Hsieh |
| 6,438,403 | B1 | 8/2002 | Cline et al. |
| 6,625,303 | B1 | 9/2003 | Young et al. |
| 6,639,965 | B1 | 10/2003 | Hsieh et al. |
| 6,674,834 | B1 | 1/2004 | Acharya et al. |
| 6,674,883 | B1 * | 1/2004 | Wei et al. ............... 382/132 |
| 6,697,451 | B2 | 2/2004 | Acharya et al. |
| 6,708,055 | B2 | 3/2004 | Geisser et al. |
| 6,789,943 | B2 | 9/2004 | Zapalac |
| 6,990,222 | B2 | 1/2006 | Arnold |
| 7,127,096 | B2 | 10/2006 | Kaufman et al. |
| 7,203,354 | B2 | 4/2007 | Wilson et al. |
| 7,251,306 | B2 | 7/2007 | Sauer et al. |
| 7,409,035 | B2 | 8/2008 | Kaufman et al. |
| 7,471,765 | B2 | 12/2008 | Jaffray et al. |
| 7,558,611 | B2 | 7/2009 | Arnold et al. |
| 7,583,778 | B2 | 9/2009 | Mori |
| 7,840,247 | B2 * | 11/2010 | Liew et al. ............... 600/407 |
| 7,970,196 | B2 | 6/2011 | Arnold et al. |
| 8,139,836 | B2 | 3/2012 | Arnold et al. |
| 2002/0196966 | A1 * | 12/2002 | Jiang et al. ............... 382/132 |
| 2003/0048867 | A1 | 3/2003 | Acharya et al. |
| 2003/0095693 | A1 | 5/2003 | Kaufman et al. |
| 2003/0120134 | A1 | 6/2003 | Rao et al. |
| 2005/0010106 | A1 * | 1/2005 | Lang et al. ............... 600/425 |
| 2007/0116345 | A1 | 5/2007 | Peterson et al. |
| 2007/0167771 | A1 * | 7/2007 | Olstad ............... 600/437 |
| 2008/0025584 | A1 | 1/2008 | Kunz et al. |
| 2008/0273652 | A1 * | 11/2008 | Arnold et al. ............... 378/4 |
| 2009/0136107 | A1 | 5/2009 | Arnold et al. |
| 2010/0012845 | A1 | 1/2010 | Baeumer et al. |

OTHER PUBLICATIONS

Baldy, R.E. et al., A Fully-Automated Computer Assisted Method of CT Brain Scan Analysis for the Measurement of Cerbrospinal Fluid Spaces and Brain Absorption Density, Neuroradiology, vol. 28, 1986, pp. 109-117.

Brown, Matthew S. et al., Knowledge-based segmentation of thoracic computed tomography images for assessment of split lung function, Medical Physics, vol. 27, No. 3, Mar. 2000, pp. 592-598.

Grashuis, J.L. et al., Semi-Automatic Contour Detection in CT-Scans of the Lumbar Spine, Proceedings of the Sixth International Workshop on Bone and Soft Tissue Densitometry, Buxton, England, Sep. 22-25, 1987, p. 33.

Greaser, L.E. 3rd et al., Electron-beam CT: the effect of using a correction function on coronary artery calcium quantitation, Acad. Radiol., vol. 6, No. 1, Jan. 1999, pp. 40-48. (one-page abstract).

Heil, Robert H., Jr., et al., Quantitative Materials Evaluation and Inspection with the Image Analysing Computer, Proceedings of the Society of Photo-Optical Instrumentation Engineers, Feb. 1972, pp. 131-143.

Kachelreiss, Marc et al., ECG-correlated image reconstruction from subsecond multi-slice spiral CT scans of the heart, American Institute of Medical Physics, vol. 27, No. 8, Aug. 2000, pp. 1881-1902.

Kalender, Willi A. et al., Vertebral Bone Mineral Analysis: An Integrated Approach with CT, Radiology, 1987, vol. 164, No. 2, Aug. 1987. pp. 419-423.

Kalender, W.A. et al., Methodological Aspects of Bone Mineral Measurements by QCT: Minimizing Operator Influence on Reproducibility, Proceedings of the Sixth International Workshop on bone and Soft Tissue Densitometry, Buxton, England, Sep. 22-25, 1987, p. 31.

Keller, James M. et al., Automatic Outlining of Regions on CT Scans, Journal of Computer Assisted Tomography, vol. 5, No. 2, Apr. 1981, pp. 240-245.

Kemerink, G.J. et al., Scanner conformity in CT densitometry of the lungs, Radiology, vol. 197, No. 3, Dec. 1995, pp. 749-752. (one-page abstract).

McCullough, Cynthia H., Ph.D., Electron-Beam CT: Use of a Calibration Phantom to Reduce Variability in Calcium Quntitation, Departments of Diagnostic Radiology and Physiology and Biophysics, Mayo Clinic and Mayo Foundation, Rochester, Minnesota, vol. 196, No. 1, Jul. 1995, pp. 159-165.

Reed, Judd E. et al., System for Quantitative Analysis of Coronary Calcification via Electron Beam Computed Tomography, Medical Imaging 1994, Physiological and Function from Multidimensional Images, SPIE, vol. 2168, Feb. 13-14, 1994, pp. 43-53.

Stoel, B.C. et al., Sources of error in lung densitometry with CT, Invest. Radiol., vol. 34, No. 4, Apr. 1999, pp. 303-309. (one-page abstract).

Wankling, P.F. et al., Computer Recognition Applied to C.T. Scans for the Automation of the Procedure for Bone Mineral Measurement Allowing Consistent Measurement Without Operator Intervention, Proceedings of the Sixth International Workshop on Bone and Soft Tissue Densitometry, Buxton, England, Sep. 22-25, 1987, p. 32.

Yoon, H.C. et al., Coronary artery calcium: alternate methods for accurate and reproducible quantitation, Acad. Radiol., vol. 4, No. 10, Oct. 1997, pp. 666-673. (one-page abstract).

General Electric, Marketing Materials distributed in 1987, four pages.

Technical Note, Automatic Outlining Technique for EMI Scanner Pictures, Medical & Biological Engineering & Computing, vol. 17, Sep. 1979, pp. 693-694.

* cited by examiner

AUTOMATIC METHOD AND SYSTEM FOR MEASUREMENTS OF BONE DENSITY AND STRUCTURE OF THE HIP FROM 3-D X-RAY IMAGING DEVICES

RELATED APPLICATIONS

The present application claims the benefit of priority under 35 USC §119(e) to U.S. Provisional Application No. 61/118,616, filed on Nov. 30, 2008, and to U.S. Provisional Application No. 61/118,619, filed on Nov. 30, 2008.

BACKGROUND OF THE INVENTION

1. Field of the Invention

The present invention is in the field of 3-D volumetric X-ray imaging, and, in particular, is directed to an automated method to measure bone density and structure of the proximal femur without operator interaction.

2. Description of the Related Art

Several diagnostic 3-D X-ray imaging devices are used in medicine to measure bone density of the hip. These imaging devices to which this invention is directed provide a set of volumetric X-ray images acquired from multiple projection angles, which allow reconstruction of images in various planes. Such devices include: dual and single energy CT scanners, rotational G-arms, X-ray tomosynthesis and 3-D DXA (dual-energy X-ray absorptiometry), in which the X-ray source is moved to provide various projections, such as the Hologic 3-D DXA device in development. In addition to bone density, other bone measurements are of interest, including cortical and trabecular bone volume, density and mass, neck cross-sectional area, neck length and angle, finite element analysis, and the like. Accurate and precise measures of bone densities of the neck and total hip regions of interest (ROIs) and their change with disease conditions or therapy has great value in detecting and treating osteoporosis. The methods disclosed herein provide improved accuracy, precision and greater ease of use for this important application.

Prior art methods have used CT scanners for bone mineral density (BMD) measurements in quantitative computerized tomography (QCT) by the use of calibration phantoms scanned simultaneously with the patient (simultaneous calibration). Such phantoms have been used for years for spinal vertebral BMD measurements and only in recent years have been used for hip BMD. Representative prior art methods are disclosed in U.S. Pat. No. 4,233,507 to Volz, U.S. Pat. No. 4,233,507 to Arnold, U.S. Pat. No. 5,335,260 to Arnold, and others, which are specific for spine measurements.

U.S. Pat. No. 6,990,922 to Arnold discloses a method for hybrid calibration using simultaneous phantom calibration along with internal tissue references of the individual patient. U.S. Pat. No. 6,990,222 is incorporated by reference herein in its entirety. Bone density measurements are known to vary significantly with different devices, over time and between different institutions, patient body compositions, imaging techniques, and, in particular, with patient positioning in hip measurements. The complicated 3-D anatomical shape, density and structure of the proximal femur make hip BMD measurements subject to variability and loss of precision with current methods. Prior art BMD methods are not applicable to the measurement of the much different anatomy of the hip. All prior art methods to our knowledge require the operator to make subjective decisions and to manually mark specific regions for measurement, or to manually mark start points for semi-automatic methods. Operator decisions and interactions are known to vary over time and between operators resulting in a loss of long term precision. Patients under drug therapy may expect to see 1 to 4% increases in BMD over the course of a year or longer of treatment. Therefore it is important to have sufficiently high precision, which will allow the clinician to reliably detect changes of this magnitude in these time periods. Prior art methods have serious limitations in achieving the desired long term precision.

Recognizing these limitations, others have reported attempts at automated methods and advanced semi-automated methods to achieve higher precisions. The most advanced methods appear to have been reported by Kang and Kang et. al in Y. Kang, *Quantitative computed tomography (QCT) of the proximal femur, Inst. of Med Physics. Erlangen*, Univ. of Erlangen, 2003, Y. Kang, K. Engelke, W A Kalender, *A new accurate and precise 3-D segmentation method for skeletal structures in volumetric CT data, IEEE Trans Med Imaging*, 2003; 22:586-98, Y. Kang, K. Engelke, W A Kalender, *Interactive 3D editing tools for image segmentation, Med Image Anal*, 2004, 8:35-46, Y. Kang, K. Engelke, C Fuchs, W A Kalender, *An anatomic coordinate system of the femoral neck for highly reproducible BMD measurements using 3D QCT, Comput Med Imaging Graph* 2005, Oct., 29(7):533-41, Epub 2005 Sep. 6, and T F Lang, G Guglielmi, C van Kuijk, A De Serio, M Cammisa, and H K Genant, *Measurement of bone mineral density at the spine and proximal femur by volumetric quantitative computed tomography and dual-energy X-ray absorptiometry in elderly women with and without vertebral fractures, Bone*, 2002 Jan., 30(1):247-50. These reported methods still require manual interactions by the operator with the images. This retains some elements of variability by the operator resulting in variable results and long term precision loss. Some of these software methods used raw Hounsfield Units (HU) and the proposed segmentation methods used single thresholds.

Since the CT numbers (HU units) are estimates of the X-ray attenuation coefficients of tissue relative to water, they fail to be truly quantitative for several reasons. The attenuation coefficients are photon energy dependent, and the X-ray beam energy spectra are not measured or known for individual patients. Further, there exist differing beam energy spectra in each image, i.e., a unique spectrum for each path length through the patient, and seen at a particular detector element and creating a unique spectrum for each view through the patient. The beam spectrum changes with the thickness and composition of tissues in the path length. These differ significantly from the shape and varied composition of real patients. Image pixel intensities vary from image to image, and are dependent on table height, position of the beam, scanner drift, tube changes, manufacturer's reconstruction software, body thickness and volume, field of view, etc.

Quantitative CT measurements of the hip with currently available commercial systems are typically facilitated by placement of a Region of Interest (ROI) within specific areas of the image to be measured, or the placement of markers at specific locations. A representative commercial system is from Mindways, Inc. The ROI or cursor marker is usually shown on a video screen as a bright line or pointer which has known X and Y locations in the image pixel matrix. The marker or ROI may be adjustable for size and/or shape and positioned by the operator in the target area on 2-D or 3-D reformatted images, by manually moving the ROI or marker under cursor control from a keyboard, by light pen or by mouse. Such manual procedures are tedious and time consuming, as well as prone to error and non-reproducibility in exact positioning. In addition, because many objects in the image, such as the trochanter or neck have complex shapes and irregular margins, a fixed geometry ROI or marker will cause errors, which can be quite large and variable and difficult to evaluate over long time periods.

Typically, the computer software uses thresholding to aid in identifying bone edges. For example, pixels anywhere in the image with HU>200 might be identified as the cortical bone edge. The operator may be required to manually place a pointer or line marker on or near the lesser trochanter or the upper end of the femoral neck region. Even though this significantly aids in locating and segmentation the bone regions, the operator, by manually placing the search marker on a 2-D representation of a complex 3-D object creates variations which reduce precision. The operator must use judgment in placing the marks or ROIs, which can lead to errors and loss of reproducibility on follow up scans attributable to human error. The ability to monitor changes in BMD is thus degraded. The automatic software methods here disclosed provide much faster exam times, more reproducible segmentations resulting in higher precision measurements.

SUMMARY OF THE INVENTION

The embodiment disclosed herein is believed to be the first totally automated hip BMD measurement method from 3-D image sets. The method is further improved by using single or dual thresholding techniques with hybrid or phantom calibrated voxels. The segmentation methods being totally automatic reduce operator time and effort while providing maximum precision. For all of the reasons discussed above, automatic identification, segmentation and quantification of bone density in the hip provides important improvements and is very desirable in the clinical setting.

Methods are disclosed which provide totally automatic measurement of hip bone density and structure from 3-D volumetric X-ray imaging devices. The methods preferably use calibrated images for improved precision, but can operate without calibration. The number of interactions by the operator with the images can be zero. The reproducibility of measurements is improved since the operator's subjective judgment is essentially eliminated. The proximal femurs are located automatically and their boundaries are identified in 3-D space.

The automated method uses criteria based on the location of the lesser trochanter, femoral head, neck angle and center-of area and automated single or dual thresholds to set anatomical locations and a 3-D coordinate system referenced to the anatomy of the specific patient. The computer software automatically determines the reproducible locations of the lesser trochanter, femoral head center-of-mass, neck minimum cross-sectional area and cortical bone margins. Adaptive level-set algorithms, region growing methods, graph cut, edge detection, Hough transform or other similar image processing methods are used to locate the 3-D cortical bone surfaces and femoral head centers. The calibration methods standardize the threshold values, which are reproducible and independent of scanner type, patient size and hip BMD.

BRIEF DESCRIPTION OF THE DRAWINGS

Without limiting the scope of the invention, the foregoing aspects and other aspects in accordance with embodiments disclosed herein are described herein in connection with the accompanying drawings, images, and figures in which.

DESCRIPTION OF THE PREFERRED EMBODIMENTS

A complete series of volumetric images making up an exam are analyzed by various computer algorithms as they are loaded into the computer. In a first preferred embodiment, an algorithm to automatically locate a calibration phantom and apply calibration of the images is completed in background mode without operator input.

Figure 1:
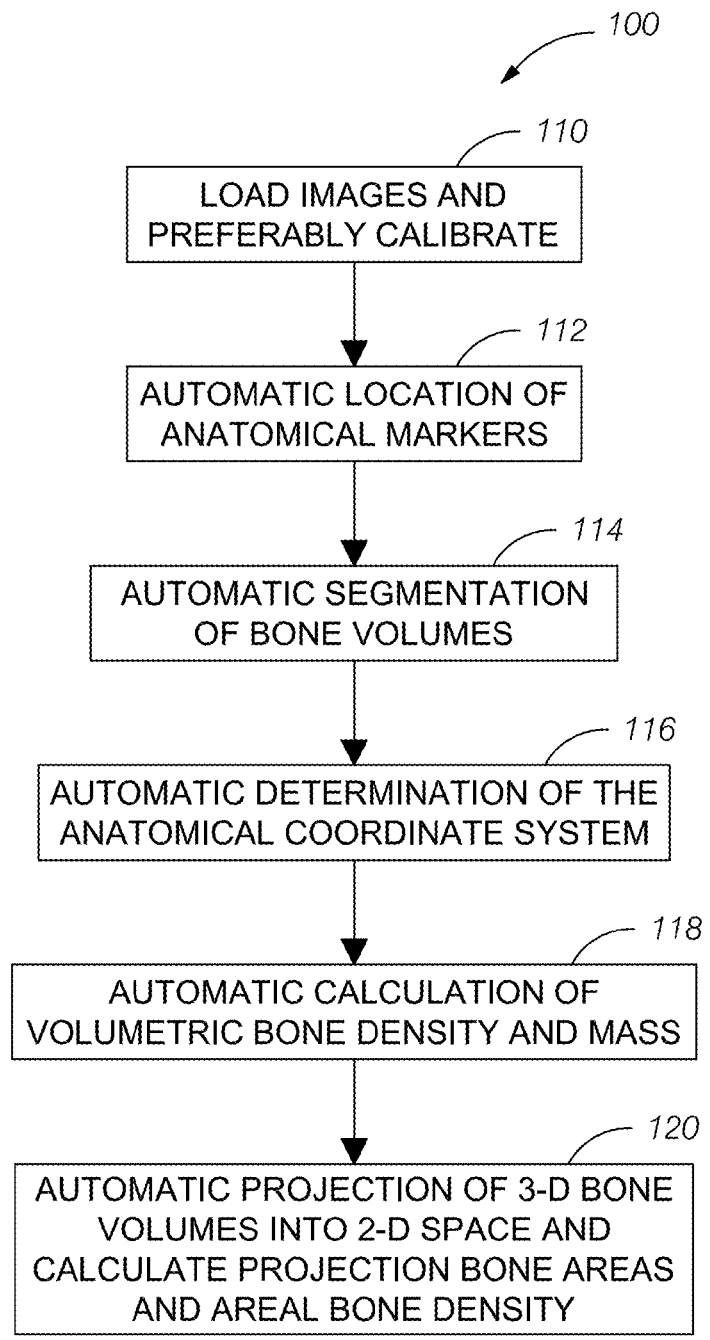
FIG. 1 illustrates a flow chart of one preferred embodiment of the disclosed invention.
Figure 2A:
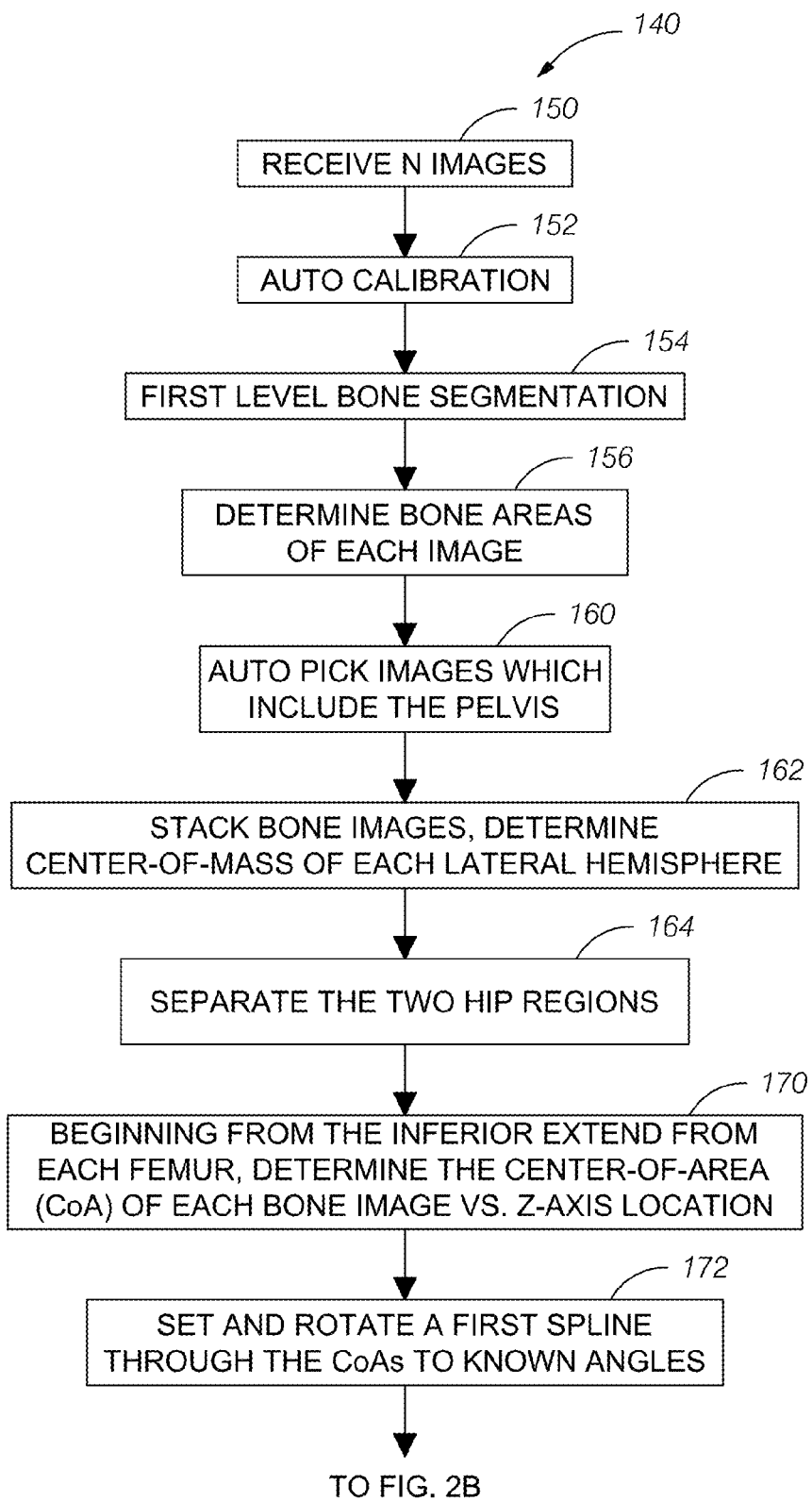
FIG. 2 illustrates a detailed flow chart of the computer software methods of the preferred embodiment
Figure 2B:
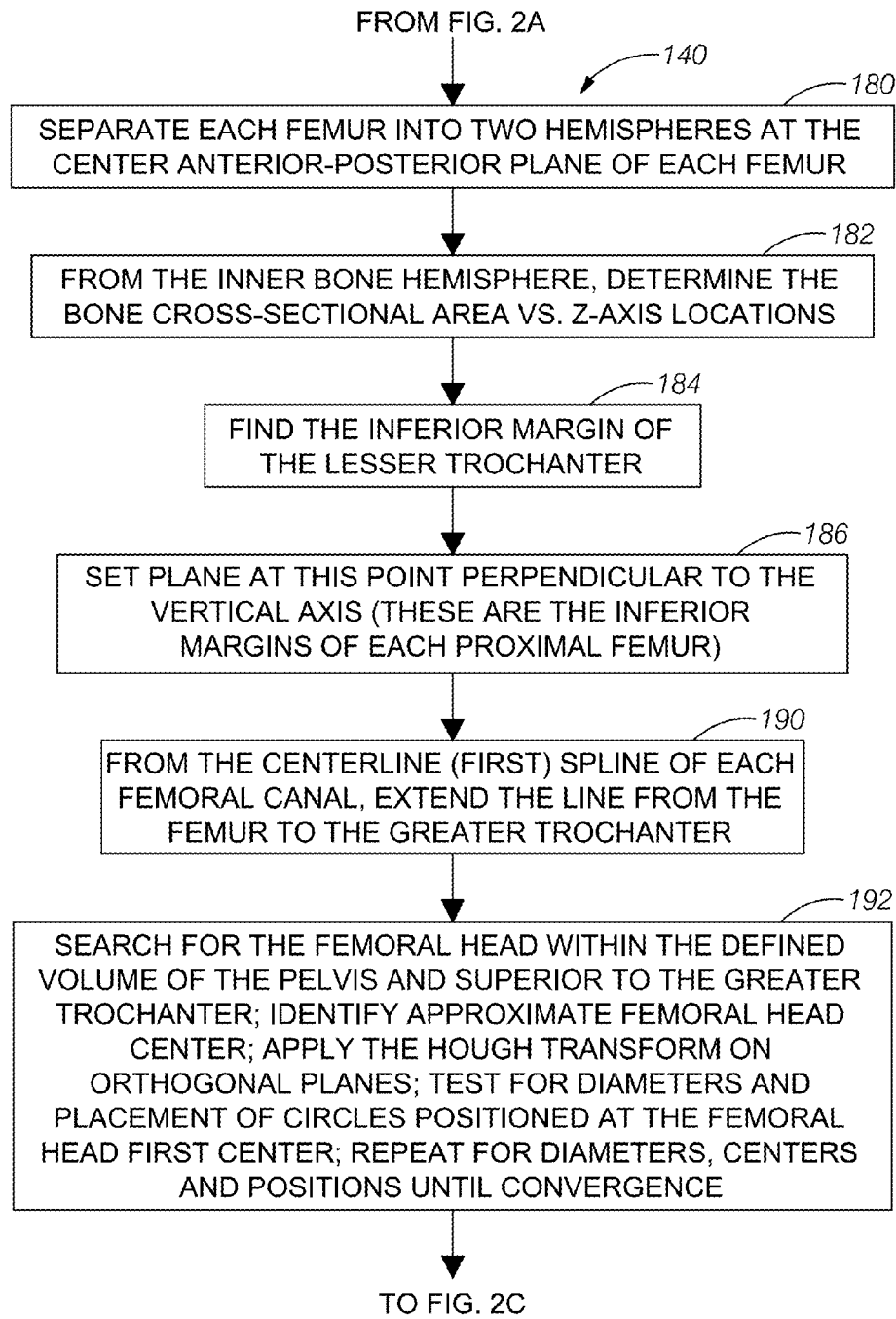
Figure 2C:
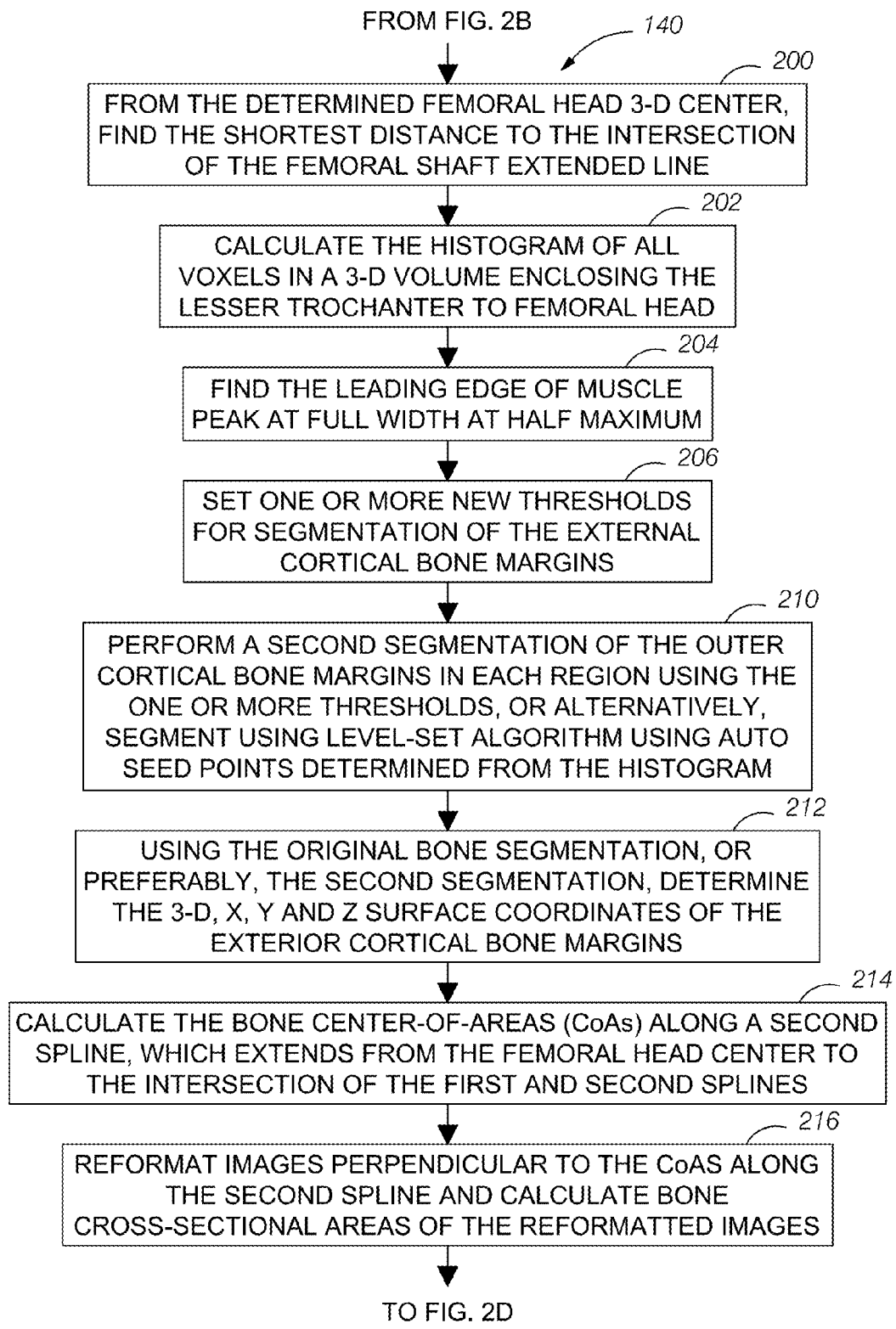
Figure 2D:
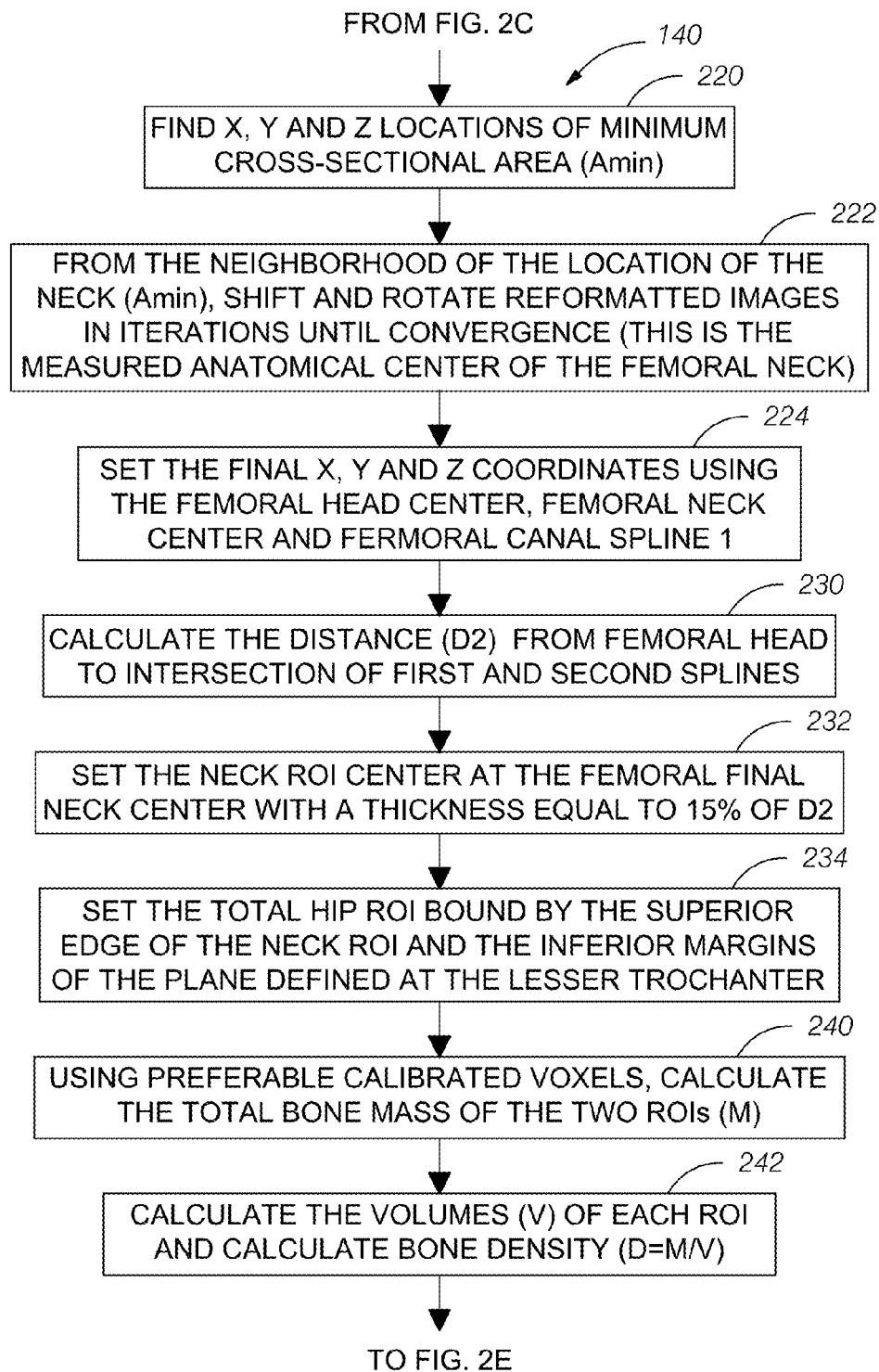
Figure 2E:
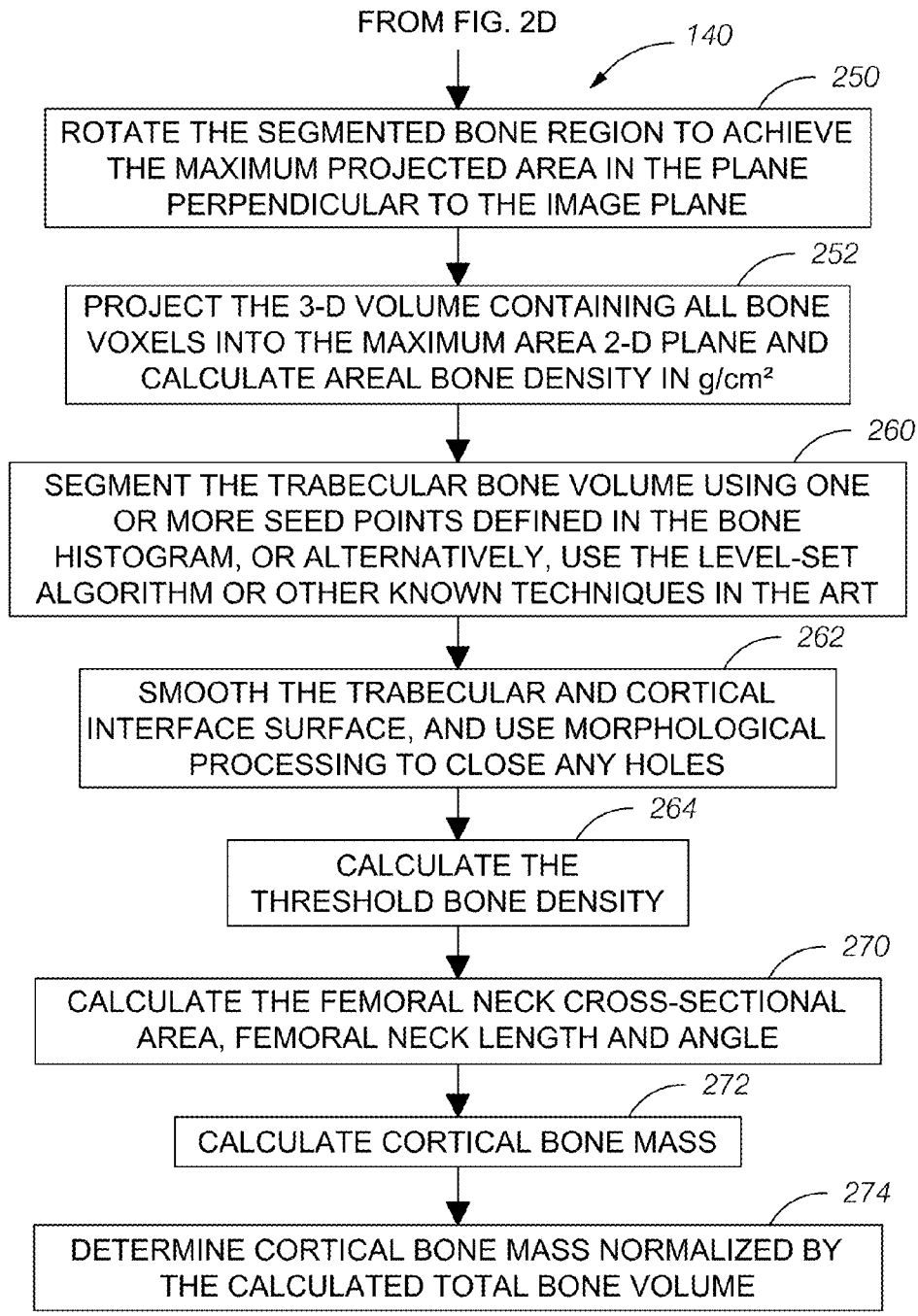

FIG. 1 illustrates a flowchart 100 of an overview of the automated methods to measure bone density of the proximal femur. In a step 110, a plurality (N) of images that include the femur are loaded. The images are generated by an imaging device shown schematically in FIG. 11 (described below). Preferably, but not necessarily, the images are calibrated with external phantoms or with the internal tissues of a subject. Preferably, the calibration occurs using the calibration equation disclosed, for example, in U.S. Pat. No. 6,990,922. For example, the calibration equation is determined by regression analysis. Through a series of automated algorithms, anatomical sites and coordinate systems markers are determined.

In a step 112, anatomical markers are automatically located. In particular, the pelvis is located by size, shape and density after removal of the overlying soft tissues. Then, in a step 114, the outer cortical margins are segmented and their extent defined by the anatomical markers at the lesser trochanter and the center of the femoral head. In a step 116, an anatomical reference coordinate system is determined based on these locations and measured angles. Then in a step 118, bone density measurements are completed for the various 3-D bone regions of interest (ROIs) and cortical or trabecular bone. In a step 120, the bone volume after rotation in the coordinate systems is projected into 2-D space and the areal bone density calculated. The measured bone densities are output in a clinical report, the result of which required no interaction with the images by the operator.

A flowchart 140 in FIGS. 2A-2E illustrates a detailed description of a segmentation operation in combination with FIGS. 3-11. In a step 150, a plurality (N) images are loaded into a computer, which may be any of several common PC computers, servers, or workstations. The images are preferably then automatically calibrated in a step 152 using the calibration equation. In certain embodiments, the calibration occurs in background mode during the loading, sorting and processing in accordance with known methods.

After the images are loaded and automatically calibrated, the method performs a first level bone segmentation in a step 154. The bone areas of each image are then determined in a step 156. The images which include the pelvis are then automatically picked in a step 160. In a step 162, the bone images are stacked, the hip regions are centered, and the center-of-mass (CoM) of each lateral hemisphere is determined. The hip regions are then separated in a step 164.

In a step 170, the method begins from the inferior extent of each femur and determines the center-of-area (CoA) of each bone image versus the Z-axis location for areas above a patient specific threshold. In a step 172, a first best-fit centerline spline is set through the CoAs, and the femur image is rotated to known angles. Preferably, when determining best-fits, the method automatically excludes deviations from circular-shaped edges.

In a step 180 (FIG. 2B), the method separates each femur into two hemispheres (a predominately inner layer hemisphere and a predominately outer layer hemisphere) at the center anterior-posterior plane of each femur. In a step 182, the method starts from the inner hemisphere and determines the bone cross-sectional area as a function of the Z-axis. In a step 184, the method further finds the inferior margin of the lesser trochanter using the deflection point of the area. In a step 186, the method sets a horizontal plane at the inferior margin. The horizontal plane is set perpendicular to a vertical axis for each proximal femur, which is determined in a step 190 by extending (extrapolating) a line from the first centerline spline of the femoral canal of each femur out beyond the greater trochanter. In a step 192, the method searches for the femoral head within the defined volume of the pelvis and superior to the greater trochanter. The approximate femoral head centers are identified, and the Hough Transform is applied on orthogonal planes. The method tests for diameters and places circles positioned at the first centers of the femoral heads. Other algorithms, such as a graph cut algorithm, may also be used to perform the tests. The method repeats the step 192 for diameters, centers and positions until convergence is reached.

In a step 200 (FIG. 2C), the method starts from the femoral head three-dimensional centers determined in the step 192 and finds the shortest distance to the intersection of the femoral shaft extended line. In a step 202, a histogram is calculated for all voxels in a three-dimensional volume that encloses the lesser trochanter to femoral head.

Figure 12:
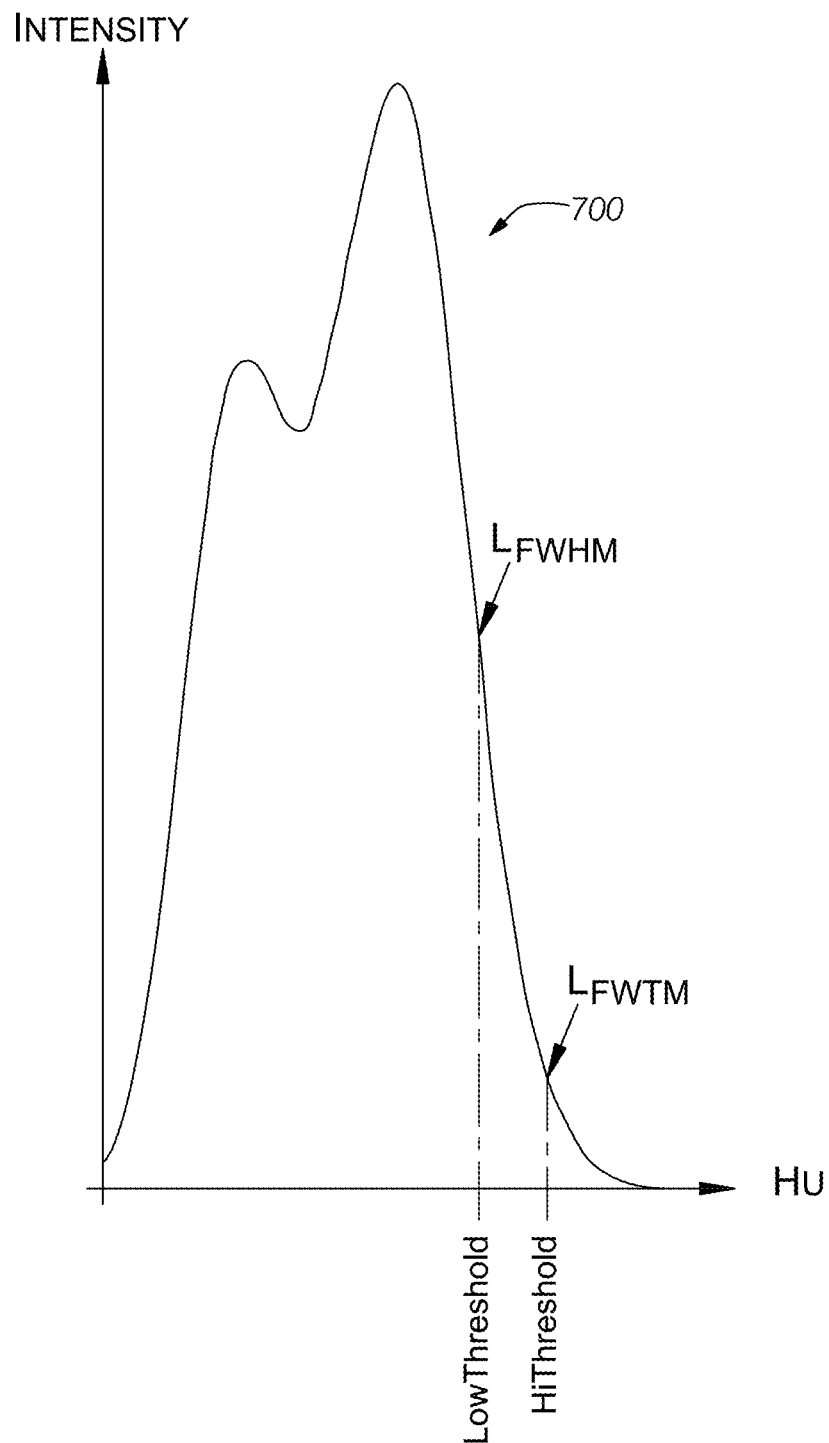
FIG. 12 illustrates a histogram of muscle density used for setting threshold values for segmentation.

In a step 204, the method finds the leading edge of a muscle peak at full width at half maximum (FWHM). The contrast between muscle and the dense cortical bone allows an excellent segmentation of the outer bone margins. In order to improve the edge definition, the method preferably determines two threshold values for use in the segmentations. The algorithm also works with a single threshold. The thresholds are set automatically by use of the muscle histogram in a step 206. For example, as illustrated for a histogram 700 in FIG. 12, one threshold, the low threshold (LowThreshold) may be set at the leading edge $L_{(FWHM)}$ at FWHM level of the muscle peak. As further illustrated in FIG. 12, a second threshold, the high threshold (HiThreshold) may be set at the leading edge $L_{(FWTM)}$ at the full width at $10^{th}$ maximum value (FWTM) of the muscle peak. The thresholds can be computed for each study as patient specific parameters by use of the equations:

$$HiThreshold = (C1 \times muscle\ density) + (C2 \times L_{FWHM} + C3);$$
and $$LowThreshold = (C4 \times muscle\ density) + (C5 \times L_{FWTM} + C6),$$

wherein C1, C2, C3, C4, C5 and C6 are constants established empirically or by theoretical computations.

The method continues in a step 210 wherein the method performs a second segmentation of the outer cortical bone margins in each region using the one or two thresholds set in the step 206. Alternatively, the method segments the margins using an adaptive level-set algorithm with auto seed points determined from the histogram.

In a step 212, the method uses either the original bone segmentation or, preferably, the second segmentation, to determine the three-dimensional x, y and z surface coordinates of the exterior cortical bone margins. In a step 214, the method calculates the CoAs of the bone and sets a second best-fit centerline spline through the CoAs from the femoral head center to an intersection of the second spline with the first spline. In a step 216, the method reformats images perpendicular to the CoAs along the second spline and calculates the bone cross-sectional areas of the reformatted images.

In a step 220 (FIG. 2D), the method finds x, y and z locations of minimal cross-sectional area (Amin). Then, in a step 222, starting in the neighborhood of the location of the neck of the femur (e.g., at Amin), the method shifts and rotates reformatted images in iterations until convergence, which determines the measured anatomical center of the femoral neck. Using the femoral head center, the femoral neck center and the first femoral canal spine, the method sets the final x, y and z coordinates in a step 224.

In a step 230, the method calculates a distance (D2) from the femoral head to the intersection of the first and second splines. In a step 232, the neck region of interest (ROI) center is set at the femoral final neck center with a thickness equal to 15% of the distance D2. A goodness-of-fit criterion is calculated based on the standard deviation of the pixel reading within the positioned ROI, which verifies centering of the ROI at or near the center of the small samples. Preferably, pixel readings at or near the edges of the samples are not used in the final calculations. In a step 234, the total hip ROI is set as bound by the superior edge of the neck ROI and the inferior margins of the plane defined at the lesser trochanter.

In a step 240, the method uses voxels, which are preferably calibrated, to calculate the total bone mass of the two regions of interest (ROIs). Then, in a step 242, the volumes (V) of each ROI are calculated, and the bone density (D) is calculated as D=M/V.

In a step 250 (FIG. 2E), the segmented bone region is rotated to achieve the maximum projected area in a plane perpendicular to the image plane. In a step 252, the three-dimensional volume containing all bone voxels is projected into the maximum two-dimensional plane and the areal bone density is calculated in grams per centimeters squared ($g/cm^2$).

In a step 260, the trabecular bone volume is segmented using one or more seed points defined in the bone histogram. Alternatively, the trabecular bone volume is segmented using the level-set algorithm or other suitable known techniques. In a step 262, the method smoothes the trabecular and cortical interface surface and uses morphological processing to close any holes. Then, in a step 264, the method calculates the threshold bone density, and in a step 270, the method calculates the femoral neck cross-sectional area and the femoral neck length and angle. In a step 272, the method calculates the cortical bone mass. In a step 274, the method determines the cortical bone mass normalized by the calculated total bone volume.

Figure 3:
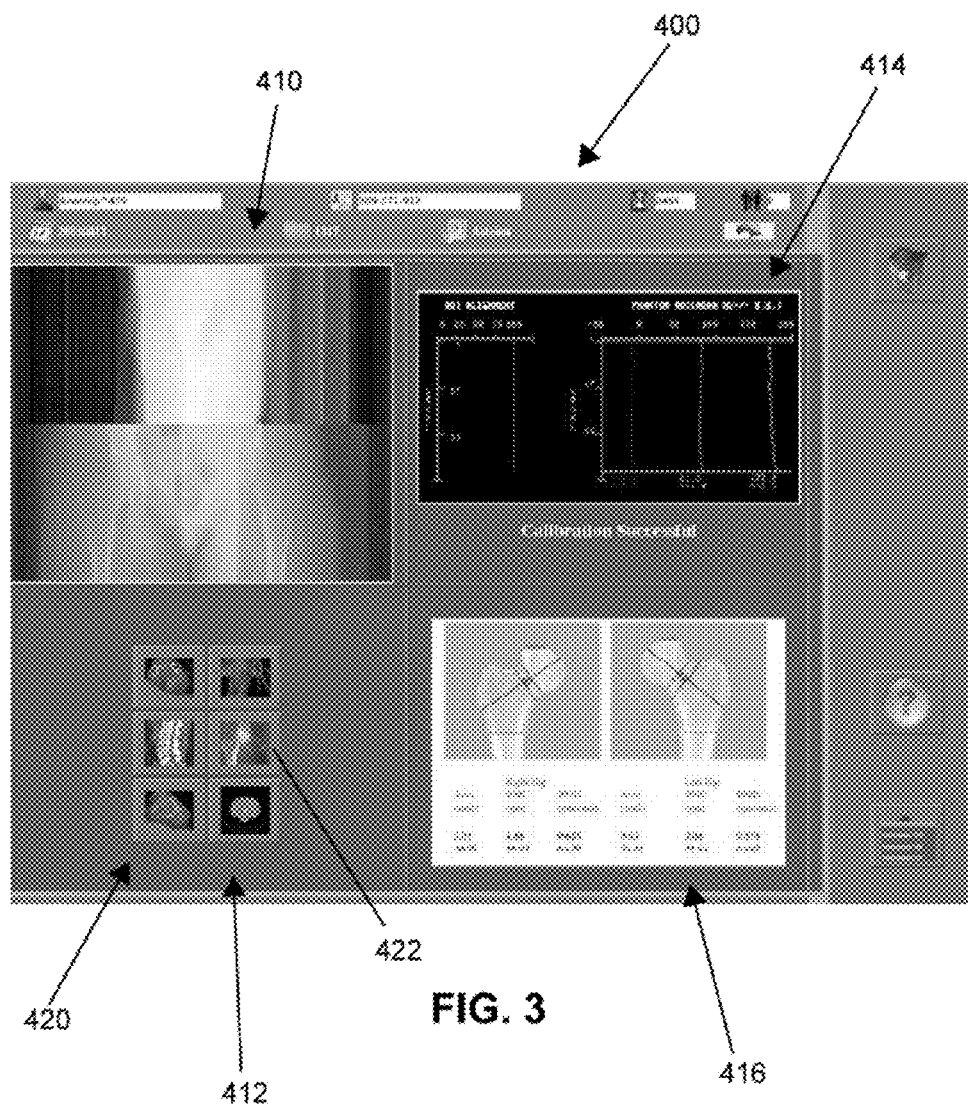
FIG. 3 illustrates an exemplary opening screen produced by the software implementation of one embodiment of the automated hip BMD method after an operator has chosen to initiate the hip BMD method from an earlier screen that allows additional selections.

FIG. 3 illustrates an exemplary display screen 400 presented by a software implementation of one embodiment of the automated hip BMD method. In particular, FIG. 3 illustrates an exemplary opening screen presented to the operator by the software after a specific patient study has been selected by the operator. The display screen in FIG. 3 includes four portions, an upper left portion 410, a lower left portion 412, an upper right portion 414 and a lower right portion 416 that present different information and control functions to the operator. For example, the lower left portion displays a 2-column by 3-row array 420 of six interactive icons that are selectable by the operator to initiate a particular application in a set of applications. In FIG. 3, the middle icon 422 in the right column was previously selected to initiate the hip BMD method, which has activated the displays shown in the other four portions of the display screen.

Figure 4:
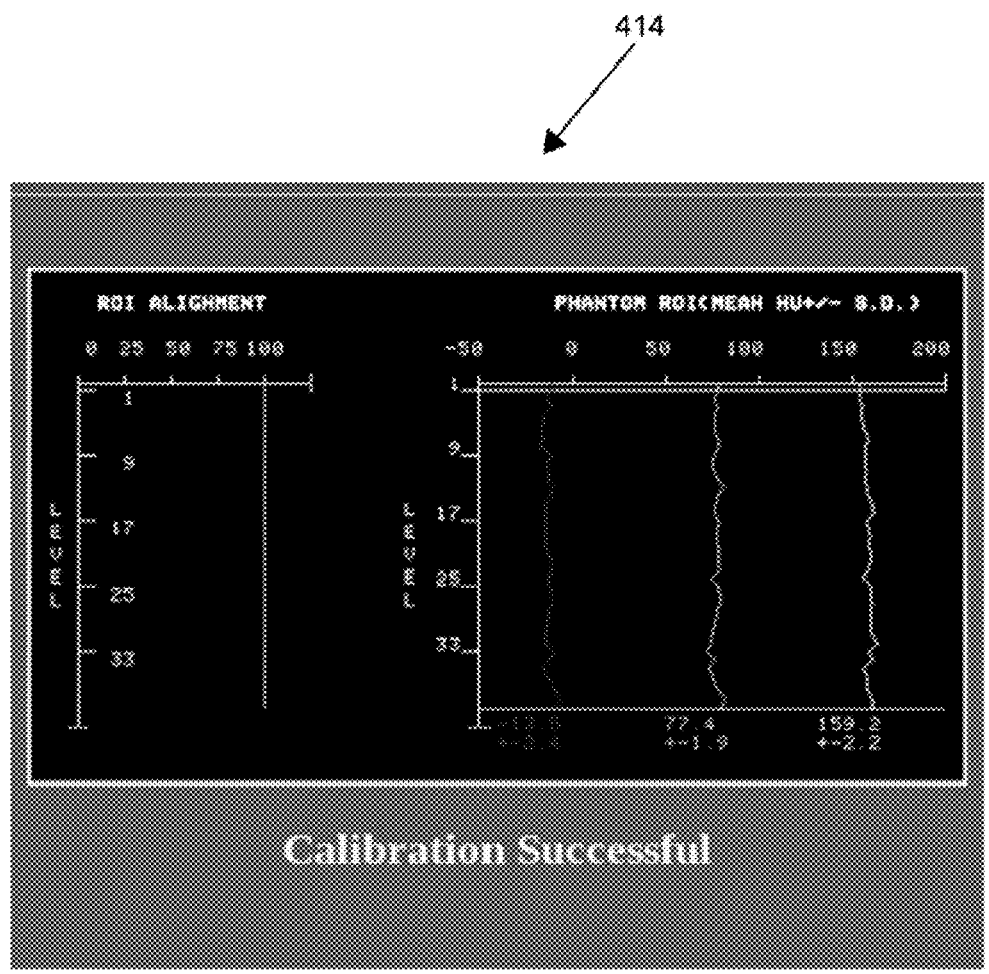
FIG. 4 illustrates a representative graph produced by the method showing the output of the automated calibration of the reference phantom readings and a figure-of-merit for correct placement of the measurement ROIs on the phantom samples.

FIG. 4 illustrates an enlarged view of the upper right portion 414 of the display screen 400 of FIG. 3, with the right portion of the view showing a representative graph generated by the method to show the output of the automated calibration of the reference phantom readings and with the left portion of the view showing a figure-of-merit for correct placement of the measurement ROIs on the phantom samples.

Figure 5:
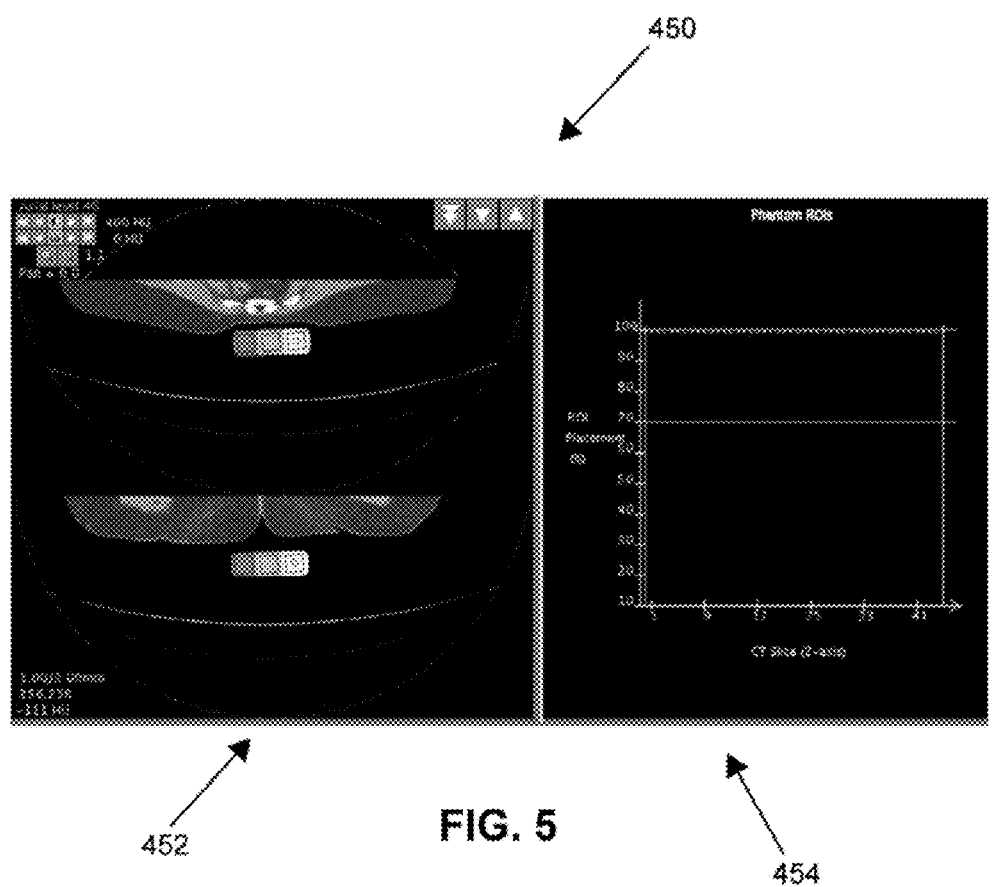
FIG. 5 illustrates a display screen having a left display portion and a right display portion, the left display portion showing the automated placement of the phantom ROIs, the right display portion showing a representative graph of the figure-of-merit computation for correct placement of the measurement ROIs in the phantom samples.

FIG. 5 illustrates a display screen 450 having a left display portion 452 and a right display portion 454, the left display portion showing the automated placement of the phantom ROIs, the right display portion showing a representative graph of the figure-of-merit computation for correct placement of the measurement ROIs in the phantom samples.

Figure 6:
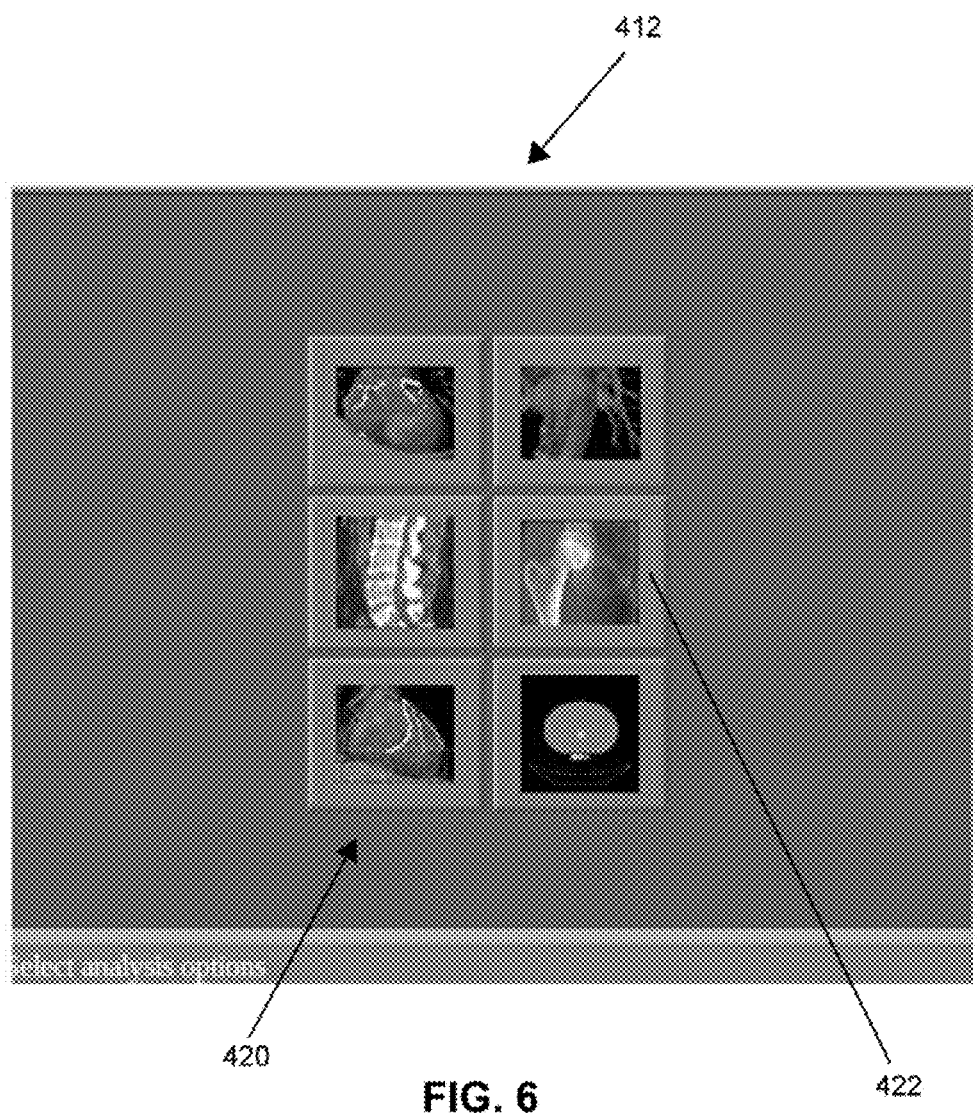
FIG. 6 illustrates the lower left screen from the automated software screen of FIG. 3 showing six icons from which the operator chooses the application to be run, wherein selection of the hip icon automatically initiates the complete hip program to achieve representative results.

FIG. 6 illustrates an enlarged view of the lower left portion 412 of the display screen 400 of FIG. 3 showing the array 420 of icons from which the operator chooses the application to be run, including the icon 422, which the operator selects to initiate the hip BMD application. Selection of the hip BMD icon in FIG. 6 automatically initiates the complete hip program to achieve representative results. The screen shown in FIG. 6 is exemplary of the software program, which use Icons instead of text throughout the program so that the system is easier to use by practitioners in any native language.

Figure 7:
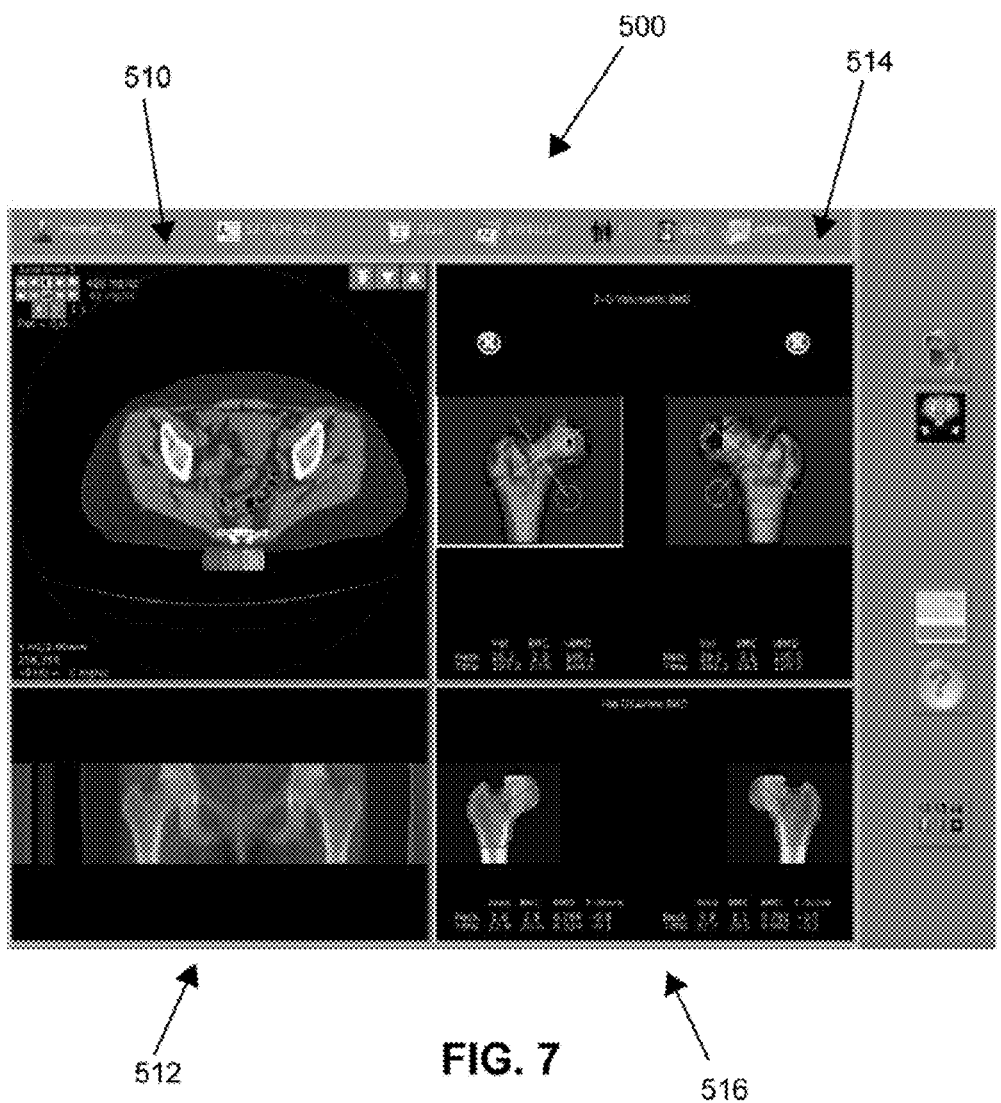
FIG. 7 illustrates an exemplary display screen having four display portions showing two views of images of the hip region in the two left portions and showing the results of the automated method selected in FIG. 6 with automatic ROI placements and bone mineral density (BMD) results in the right two portions.

FIG. 7 illustrates a display screen 500 that shows the results of the automated method selected in FIG. 6 with Auto ROI placements and BMD results. The display screen in FIG. 7 includes four portions with an upper left portion 510 showing an image of an elevational slice through the pelvic area, with a lower left portion 512 showing an image with a plan view of a portion of the pelvic area, with an upper right portion 514 showing a 3-D volumetric view of the proximal femurs and calculated volumetric data, and with a lower right portion 516 showing a calculated cross-sectional view of the proximal femurs and calculated areal data.

Figure 8:
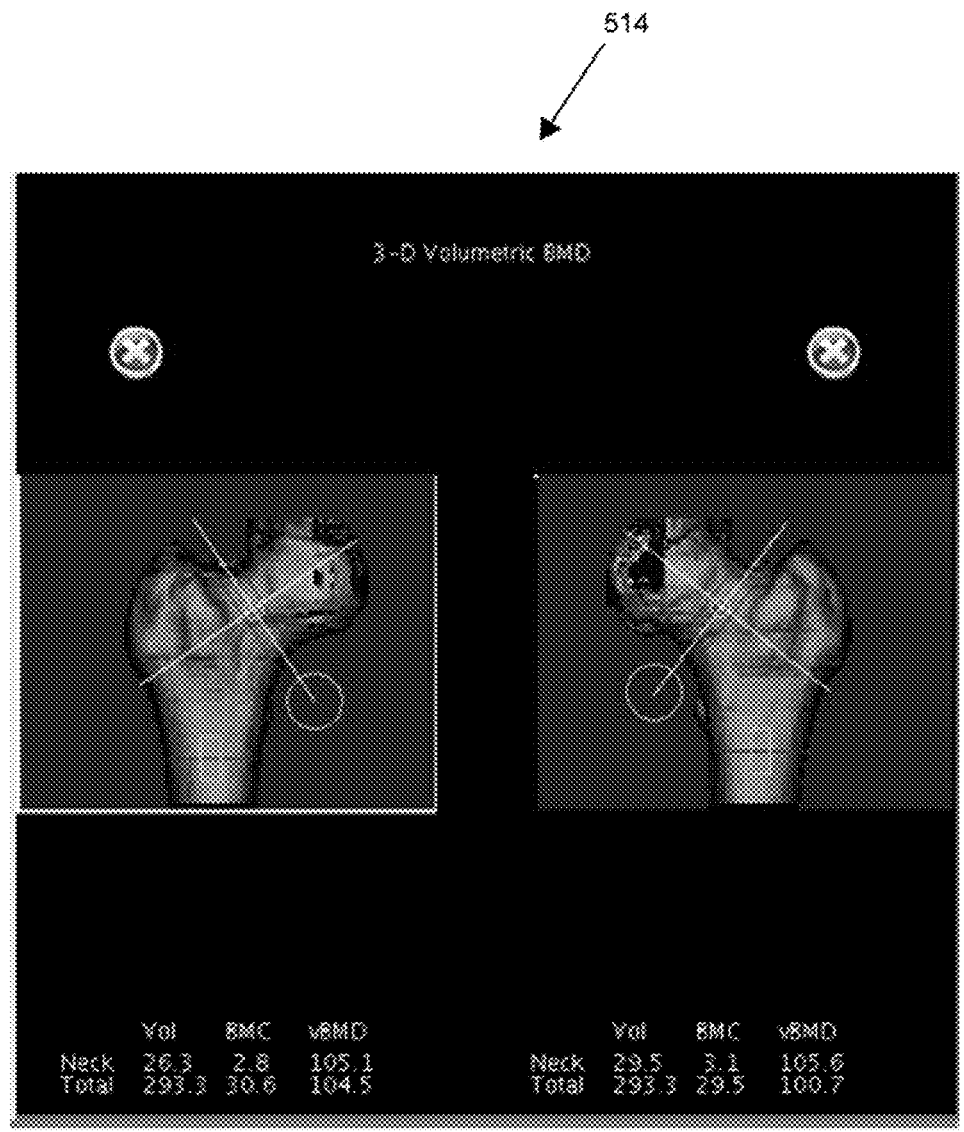
FIG. 8 illustrates the upper right portion of the display screen of FIG. 7 in more detail.

FIG. 8 illustrates the upper right screen 514 of FIG. 7 in more detail showing the marker at the lesser trochanter, showing the neck ROIs and showing the coordinate system set to the anatomy of each of the patient's proximal femurs, wherein the integral volumetric BMD results are shown at the bottom. In FIG. 8, the volume, bone mineral content and the resulting volumetric bone densities of the neck ROI and total hip regions are shown.

Figure 9:
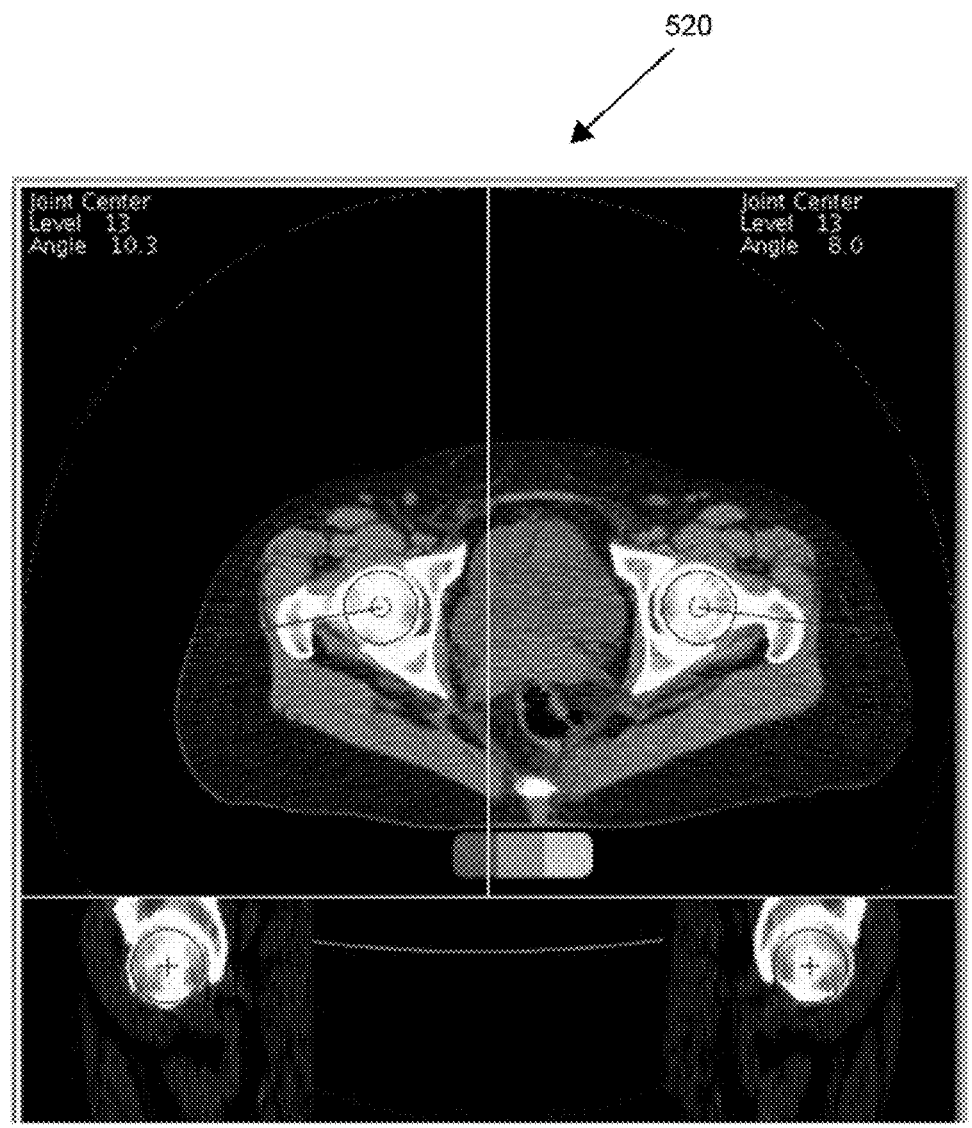
FIG. 9 illustrates a screen display showing the manual function available if the operator wants to adjust the rotations or axis centering.

FIG. 9 illustrates a display screen 520 which presents an operator with a manual function that enables the operator to optionally adjust the rotations or axis centering.

Figure 10A:
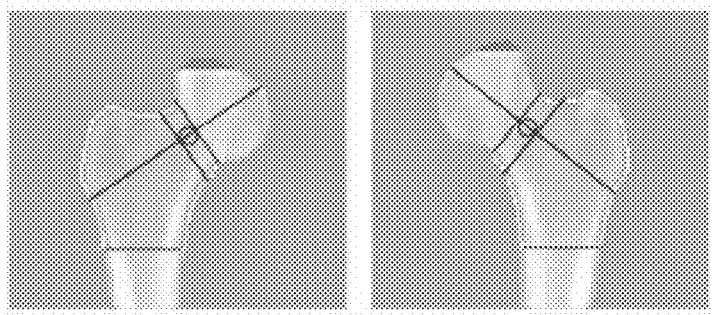
FIG. 10A illustrates a clinical report with 2-D projected BMD readings along with ROI placements, BMD readings for each hip, BMD averages and the calculated T-zones and Z-scores.
Figure 10B:
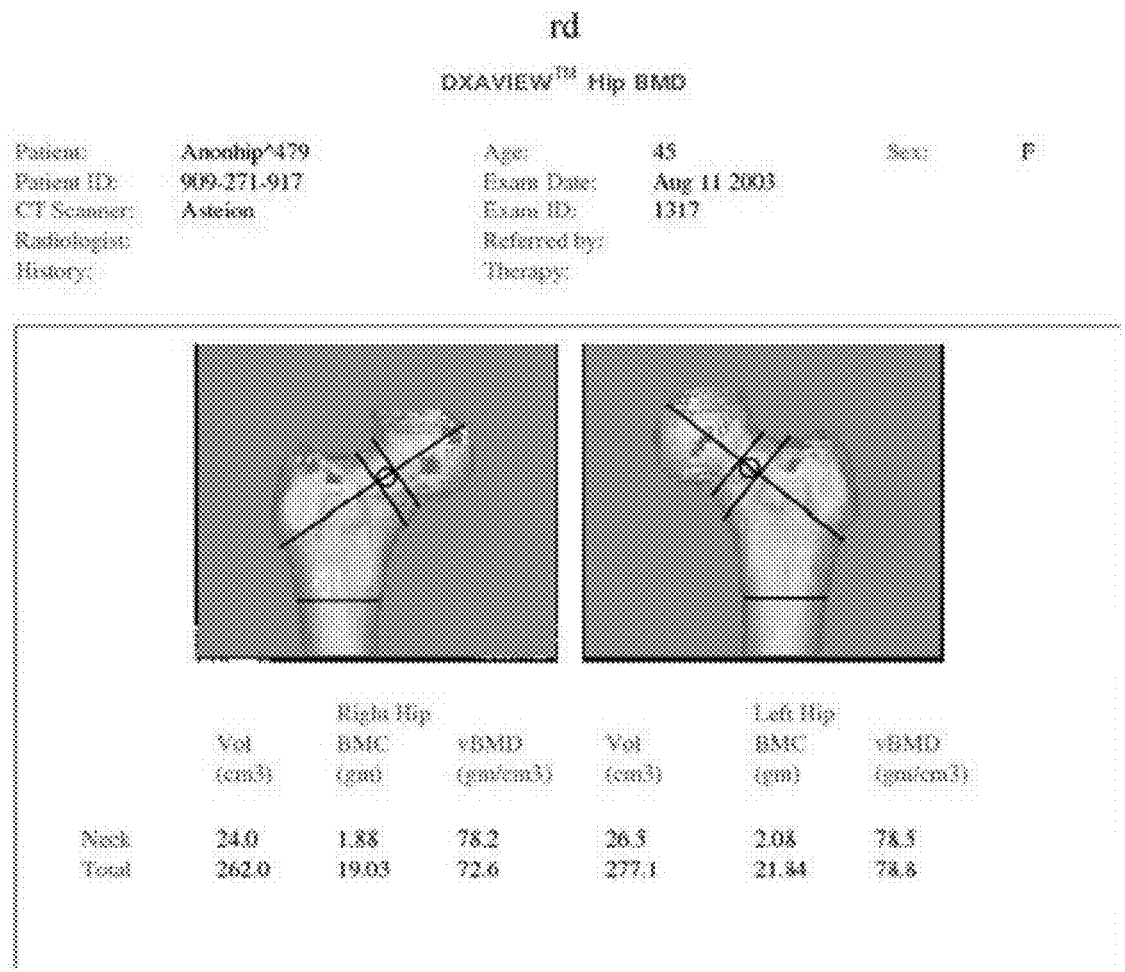
FIG. 10B illustrates a similar clinical report that shows the volumetric BMD results.

FIG. 10A illustrates the clinical report with 2-D projected BMD readings along with ROI placements, areal BMD readings for each hip, BMD areal averages and the calculated T-zones and Z-scores. FIG. 10B illustrates a similar clinical report showing the volumetric (3-D) BMD results based on the same input images.

Figure 11:
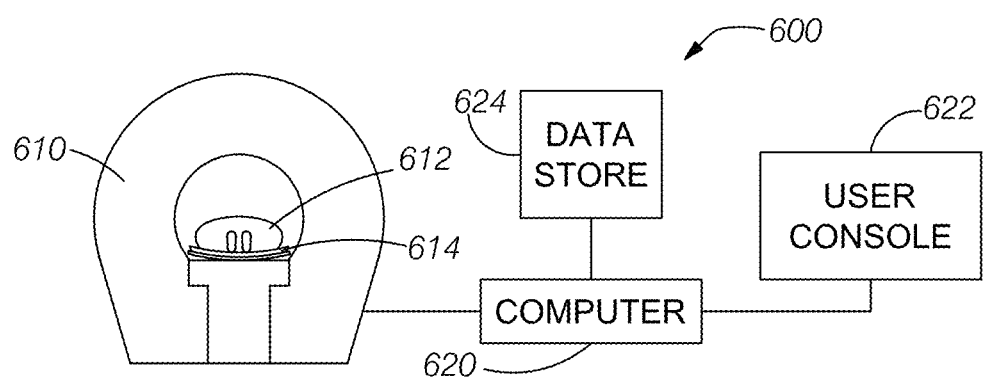
FIG. 11 illustrates a block diagram of an exemplary system for implementing the method disclosed herein.

FIG. 11 illustrates a block diagram of an exemplary system 600 for implementing the method disclosed herein. As illustrated, an imaging device 610 scans a patient 612 and a calibration reference 614 simultaneously to generate image data. The image data generated by the imaging device is coupled to a data processing (computer) system 620. The imaging device and the computer system may be coupled directly as shown or may be coupled indirectly through an intermediary data storage system (not shown). Accordingly, the method disclosed herein may operate on currently scanned images or on previously scanned and stored images. As further illustrated in FIG. 11, the computer system is coupled to a user's console 622 and to a data storage unit 624. One or both of the user's console and the data storage unit may be integrated with the computer system or may be external devices as illustrated. The computer system is responsive to instructions to perform the method disclosed herein and thereby operate on the raw or preprocessed image data to generate the images and the volumetric and areal density information as described above.

One skilled in art will appreciate that the foregoing embodiments are illustrative of the present invention. The present invention can be advantageously incorporated into alternative embodiments and a variety of imaging devices which produce axial images or volumetric scans while remaining within the spirit and scope of the present invention, as defined by the appended claims.

The invention claimed is:

1. A method to measure bone density and structure of the proximal femur of the hip of an individual subject from images acquired with a three-dimensional (3-D) X-ray imaging device, the method comprising:

providing 3-D images acquired from a 3-D X-ray imaging device to a computer programmed with image processing software;

automatically identifying the pelvis and the left hip and the right hip including a volume of bone that includes the femoral head and lesser trochanter of each hip;

automatically identifying the femoral head of at least one hip as an anatomical marker of the at least one hip;

automatically determining a 3-D center of the femoral head of the at least one hip by applying the Hough Transform in at least one plane by the computer executing the software to analyze voxels of the 3-D images without operator interaction;

automatically finding the lesser trochanter of the at least one hip by computing the cross-sectional areas of bone along a femoral shaft;

automatically computing an anatomical center of the femoral neck by iteratively reformatting the images and computing cross-sectional bone areas along the femoral neck to converge on the anatomical center;

automatically positioning a neck region of interest (ROI) at the anatomical center of the femoral neck;

automatically positioning a hip ROI bounded by the neck ROI and the lesser trochanter; and automatically determining bone density and bone structure measures of the regions by the computer executing the software.

2. The method of claim 1, wherein the three-dimensional x-ray imaging device is a 3-D dual energy x-ray absorptiometry (DXA) machine.

3. The method of claim 1, wherein one of the bone density measures is the cortical bone mass.

4. The method of claim 1, wherein the three-dimensional imaging device is a computed tomography (CT) scanner.

5. The method of claim 1, wherein the computer executing the software automatically positions the hip ROI using two image intensity thresholds to identify the bone regions.

6. The method of claim 5, wherein at least one of the thresholds is calculated by the computer executing the software using a measure of the intensity of images of the muscle of the subject.

7. The method of claim 1, wherein the bone structure measures are cross-sectional dimensions of bone structures.

8. The method of claim 1, wherein the bone density measures are calibrated by the computer executing the software to analyze images created by imaging a phantom independent of the subject using the three-dimensional X-ray imaging device.

9. An automatic method to measure bone density of the hip in a subject using x-ray computed tomography (CT) by acquiring a volumetric set of three-dimensional CT images containing voxels representing x-ray attenuation of the subject, the method comprising:

providing a volumetric set of three-dimensional CT images containing voxels to a computer programmed with image processing software, the volumetric set of three-dimensional CT images including voxels that represent a hip of the subject;

executing the software in the computer to automatically locate a margin of the lesser trochanter and the femoral head of at least one hip as patient specific anatomical markers of the hip;

automatically locating a three-dimensional (3-D) center of the femoral head;

automatically locating the centerline of the femoral neck extending from the femoral head to the greater trochanter by the computer executing the software to analyze voxels of the 3-D images without operator interaction;

automatically locating the centerline of the femoral shaft extending from the lesser trochanter to the greater trochanter of the hip;

automatically positioning a neck region of interest (ROI) at the anatomical center of the femoral neck by computing the bone areas along the centerline of the femoral neck;

executing the software in the computer to automatically identify a 3-D hip ROI volume which includes trabecular bone of the hip bounded by the neck ROI and the margin of the lesser trochanter;

executing the software in the computer to automatically analyze the hip 3-D ROI volume to identify voxels which satisfy defined conditions; and executing the software in the computer to automatically evaluate the identified voxels in the hip 3-D volume to determine a measure of bone density.

10. The method of claim 9 wherein the defined conditions include one or more thresholds and 3-D connectivity criteria.

11. The method of claim 9, wherein the identified voxels in the three-dimensional ROI volume contain muscle or fat.

12. A method to measure properties of the proximal femur of the hip of an individual subject from images acquired with a three-dimensional (3-D) imaging device, the method comprising:

providing 3-D images acquired from a 3-D imaging device to a computer programmed with image processing software;

automatically locating the external cortical bone margins of at least one hip by the computer executing the software to analyze voxels of the 3-D images without operator interaction;

automatically locating the lesser trochanter by computing the areas enclosed by the cortical bone margins along the femoral shaft of the femur;

automatically locating a 3-D reference point of the lesser trochanter as a first specific anatomical marker of the subject's hip by the computer executing the software to analyze voxels without operator interaction;

automatically locating the femoral head by computing geometrical measures of the 3-D volume enclosed by the cortical bone margins;

automatically locating the 3-D center of the at least one femoral head as a second specific anatomical marker of the subject's hip by the computer executing the software to analyze voxels of the 3-D image without operator interaction;

automatically positioning at least one 3-D ROI to encompass a volume of bone defined by the cortical margins and the first and second subject specific anatomical markers; and automatically determining one or more properties of the bone volume in the hip 3-D ROI by the computer executing the software.

13. The method of claim 12, wherein the properties of the bone volume include the volume of bone.

14. The method of claim 12, wherein the properties of the bone volume include bone cross-section areas at locations in the volume of bone.

15. The method of claim 12, wherein the properties of the bone volume include cortical bone mass.

* * * * *